United States Patent
Nurcombe

(10) Patent No.: US 7,143,631 B2
(45) Date of Patent: Dec. 5, 2006

(54) OLFACTORY METHOD FOR ASSESSING QUANTITATIVE AND QUALITATIVE ODOR CHARACTERISTIC IN AN AIRSTREAM

(75) Inventor: Claire Nurcombe, Hamburg (DE)

(73) Assignee: Airbus Deutschland GmbH (DE)

( * ) Notice: Subject to any disclaimer, the term of this patent is extended or adjusted under 35 U.S.C. 154(b) by 7 days.

(21) Appl. No.: 11/021,857

(22) Filed: Dec. 23, 2004

(65) Prior Publication Data
US 2005/0141668 A1  Jun. 30, 2005

(30) Foreign Application Priority Data
Dec. 29, 2003 (EP) ................... 03029923

(51) Int. Cl.
*G01N 7/00* (2006.01)
*G01N 33/497* (2006.01)

(52) U.S. Cl. .................... 73/23.34
(58) Field of Classification Search ............ 73/23.34; 702/199
See application file for complete search history.

(56) References Cited

U.S. PATENT DOCUMENTS 3,815,405 A * 6/1974 Dravnieks ............ 73/23.34
6,018,984 A * 2/2000 McGinley et al. ...... 73/23.34
6,463,786 B1* 10/2002 Behan et al. .......... 73/23.34

FOREIGN PATENT DOCUMENTS

DK  WO9102972 * 7/1991

OTHER PUBLICATIONS

Persuad, K.C. et al., "Measurment of sensory quality using electronic sensing systems", Measurement and Control, Feb. 29, 1996.*
Bkuyssen, M Dr. Philomena, "Air Quality Evaluated with the Human Nose," Air Infiltration Review, vol. 12, No. 4, Sep. 1991, p. 5-9.*

(Continued)

*Primary Examiner*—Hezron Williams
*Assistant Examiner*—Ryan Christensen
(74) *Attorney, Agent, or Firm*—Ostrolenk, Faber, Gerb & Soffen, LLP

(57) ABSTRACT

An olfactory method for simultaneously assessing a quantity and a quality of odors in an airstream, comprising the steps of determining a first mean value of results of ratings of an acceptability of an odor of a single airstream, rated by a group of test persons; determining a second mean value of results of ratings of an odour intensity done by the same group of test persons for the same odorous airstream; determining a decipol value of ratings of a perceived air quality according to the method of Fanger of the same odorous airstream, rated by the same group of test persons; providing a matrix containing all mathematically possible values of the acceptability of rating, the odor intensity rating and the decipol values of the perceived air quality, wherein each value or a range of values of one the three rating categories is assigned to one score in a scale of scores: determining a score for each of the values taken from steps a), b), and c) by classifying it into one of the values or ranges of values in a corresponding category in the matrix of step d), which results in three scores; and calculating a third mean value of the three scores, resulting in an overall average score corresponding to an overall quantitative and qualitative odor characteristics of the airstream evaluated.

5 Claims, 1 Drawing Sheet

OTHER PUBLICATIONS

European Search Report, Appl. No. EP 03 02 9923, dated Jul. 7, 2004.

Henderson H I Jr. et al. "The impact of comfort control on air conditioner energy use in humid climates" (Abstract), citation form Database Compendex, Engineering Information, Inc., New York, N.Y., USA; Database Accession Nos. EIX93091640036 and XP2285504.

Persaud, K.C. et al. "Measurement of sensory quality using electronic sensing systems" (Measurement and Control) vol. 29, Feb. 1996, pp. 17-20.

VDI 3882 Part 1 (edition 10/92) "Olfactometry; Determination of Odour Intensity", Verein Deutscher Ingenieure, Düsseldorf (1992), total pages 29.

VDI 3882 Part 2 "Olfactometry Determination of Hedonic Odour Tone", Verein Deutscher Ingenieure, Düsseldorf (1992), total pages 19.

Fanger, P.O., "Introduction of the olf and the decipol Units to Qualify Air Pollution Perceived by Humans indoors and Outdoors" Energy and Buildings (1998) Elsevier Sequoia/Printed in the Netherlands, total pages 6.

* cited by examiner

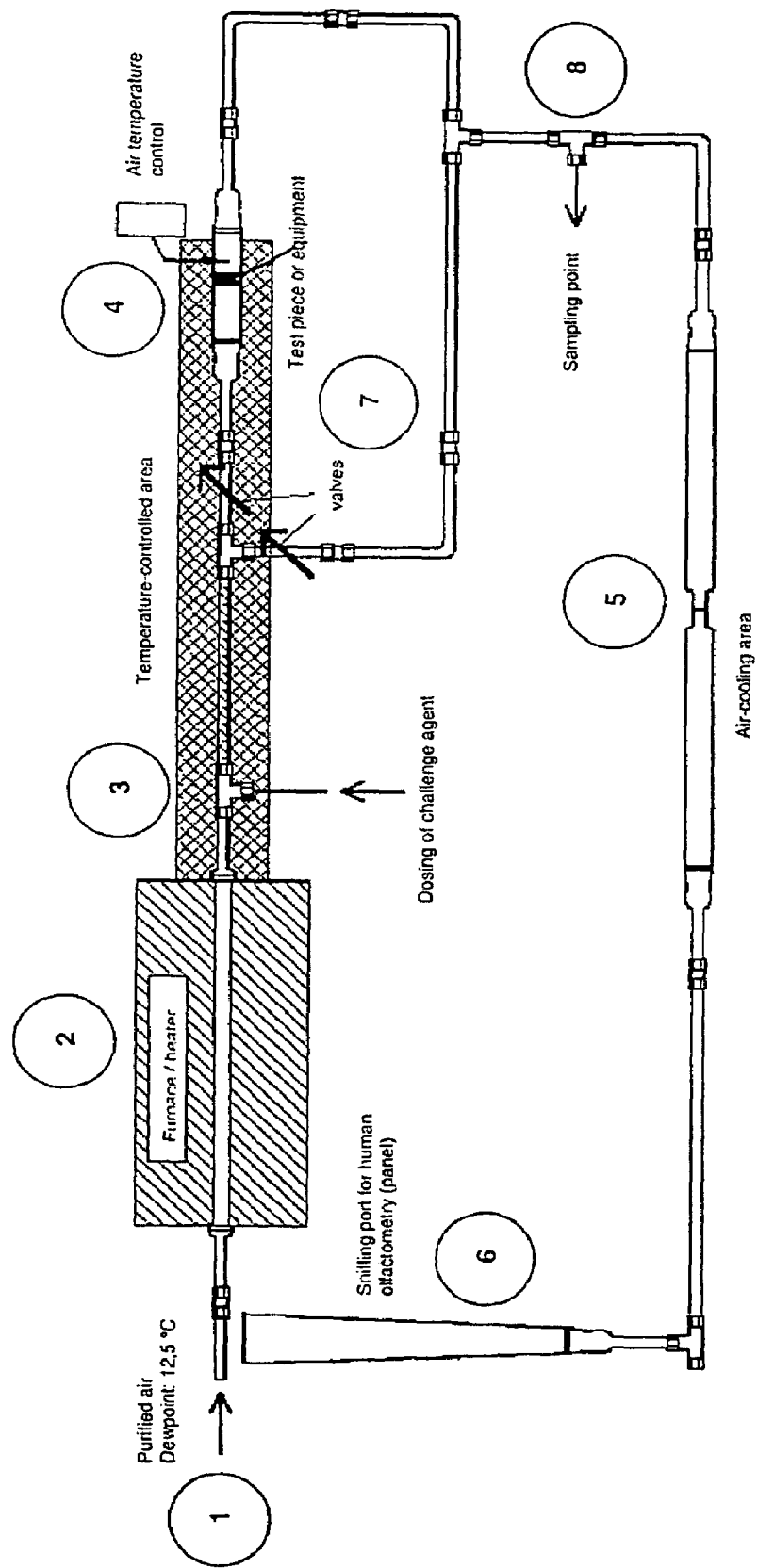
Figure 1 – Experimental Test Bench

OLFACTORY METHOD FOR ASSESSING QUANTITATIVE AND QUALITATIVE ODOR CHARACTERISTIC IN AN AIRSTREAM

FIELD OF THE INVENTION

The present invention is directed to an olfactory method for simultaneously assessing the quantity and the quality of odours in an airstream.

TECHNICAL BACKGROUND

Typically, the discernment and evaluation of odours is performed by the olfactory sense of the human being. By this method, it must be considered that different persons or panels have different olfactory sensitivities and the olfactory sense of a panel may vary depending on such mitigating factors as mood, alertness, health, etc. of the panel on the day of the test. Therefore, to obtain an objective result with high systematic accuracy, it is necessary to gather an adequate number of persons and to conduct the test under an adequately uniform environmental condition. Typically, current methods for assessing odour include the use of panels of untrained people to qualify the odour characteristics (tone, intensity and overall perceived air quality) as per VDI 3882/2, VDI 3882/1 and Fanger's decipol calculation method (Fanger, 1988, "Introduction of the olf and the decipol units to quantify air pollution perceived by humans indoors and outdoors", Energy and Buildings, 12, 1–6, the disclosure of which is incorporated herein by reference).

However, these methods have not been used for overall odour quantification, and thus using the existing methods of analysing the results, comparisons of odour removal performance of equipments used to remove unpleasant odours from an airstream are not possible.

In aircraft cockpits and cabins unpleasant odours leading to discomfort of the crew and passengers often originate from so-called VOCs (Volatile Organic Compounds) that lead to these odours. VOC contamination in the aircraft cabin inlet airstream often stem from ground operations of the aircraft, such as push back, taxiing, etc., by which the airport air may be contaminated by the engine exhaust fumes, fuel fumes and other air borne contaminants. These contaminants are ingested by engines and Auxiliary Power Units and may lead to contamination of the bleed air supply.

There are several recognised methods by which the engine exhaust fumes and fuel fumes can be ingested into the aircraft cockpit and cabin, for example during ground operations when taxiing behind another aircraft or in the queue for take off VOC-containing airstreams enter the aircraft cockpit and cabin. Furthermore, certain wind conditions at engine shut down if the Auxiliary Power Unit has already been started or during ground operations the exhaust fumes of the ground service vehicles may also lead to an ingestion of contaminated air by the Auxiliary Power Unit.

Several different types of equipment are currently proposed to remove VOC that lead to these unpleasant odours in the cabin or cockpit air. However, while there are means by which the efficiency in removing these VOCs can be measured, there is no recognised method by which the efficiency in reducing the odour due to the VOCs can be quantified. It is often the case that strong and unpleasant odours may be attributed to very small amounts of some specific VOCs, whereas larger amounts of others do not significantly contribute to unpleasant odours. At present, it is impossible to accurately assess the claims of available technology in the field of odour reduction.

SUMMARY OF THE INVENTION AND EXEMPLARY EMBODIMENTS

Therefore, there is a need for a reliable test and analysis method allowing for a simultaneous assessment of the quantity of the quality of odours in an airstream, which allows, for example, a direct comparison of equipment used for removing VOCs from an airstream, when tested under the same conditions.

The olfactory method outlined in this patent application allows overall odour characteristics to be qualified and quantified simultaneously, allowing the performance of different odour removal methods to be compared with each other and to be evaluated. The inventive method is also compatible with other test methods, such as FID (Flame Ionisation Detection) and GC-O (Gas Chromatography-Olfactometry), allowing total hydrocarbon detection, or individual odour compounds to be analysed.

The solution provided by the inventive method is based on the results of panel tests with the use of untrained participants. Additionally, analytical tests using GC-O and/or FID may also be carried out in parallel or subsequently.

According to the inventive method according to an exemplary embodiment, it is first necessary to determine numerical values representing the acceptability of an odour, the odour intensity, and the perceived air quality.

To obtain such values, a panel test may be performed. Normally, untrained panellists are chosen to rate the airstream for odour tone, odour intensity and the overall perceived air quality. The number of panellists should be sufficient to achieve a statistical significance of the results obtained. The skilled person will choose an appropriate number of panellists as necessary to obtain statistically significant results. The total number of panellists will thus be an arbitrary number. According to the present invention, it is preferred to use at least 30 or more untrained panellists. These panellists rate the air upstream and downstream of a catalyst or equipment used to remove VOCs from an air stream to allow a percentage change in the odour parameters due to the catalyst or the equipment used to be determined. Independently of any equipment used to remove VOCs, the analysis may rate any airstream provided to them from any origin in order to assess the odour characteristics of the airstreams to be evaluated.

The three categories of odour characteristics used in the present invention are as follows:

i) Hedonic Tone

Hedonic tone rates the acceptability of the odour on a given scale which is attributed to a range of odour characteristics from extremely unpleasant to extremely pleasant. For example, a nine-point scale may be used, from −4 to +4. On this scale −4 corresponds to extremely unpleasant, +4 to extremely pleasant, and 0 is the point at which the odour changes from unpleasant to pleasant.

ii) Odour Intensity

Odour intensity rates the strength of the an odour also on a scale providing a rating of the odour strength from an undetectable odour to an extremely strong odour. For example, a seven-point scale from 0 to +6 may be used, wherein 0 corresponds to an undetectable odour and +6 to extremely strong odour.

iii) Perceived Air Quality

The measure of perceived air quality was developed to allow the overall air quality in a room to be evaluated. According to the method of Fanger, see above, the air quality is measured in decipol on a scale from 0 to +31.

0 decipol corresponds to 100% of the panel members being satisfied and 31 decipol corresponds to 100% of panel members being dissatisfied. The relationship between decipol and percentage of satisfied panel membes is not linear. The disclosure of the article of Fanger in Energy of Buildings, 12,1 to 6, 1988, is incorporated herein by reference.

A skilled person will be well aware of the fact that any kind of scale may be used for rating any of the above-mentioned odour characteristics and that the present invention is not restricted to any specific type of scale.

Once the panellists have rated an airstream according to the three categories mentioned above, a mean value for the results of ratings of acceptability of the odour (the hedonic tone) of the single airstream evaluated is calculated. Similarly, the mean value of the odour intensity ratings of the analysis for the same odourous airstream is calculated. Thirdly, the decipol value of the ratings of the perceived air quality according to the method of Fanger are the same odourous airstream and rated by the same group of test persons or panellists is also determined.

In a next step of the present invention, a matrix is provided, which contains all possible mathematically possible values of the acceptability rating, the odour intensity rating and the decipol values of the perceived air quality, wherein each value or range of values of one of the three above-mentioned rating categories is assigned to one score in a scale of scores.

In a next step, the score for each of the values determined from the panellists' ratings in the three categories, namely, the first mean value of the acceptability ratings, the second mean value of the odour intensity ratings and the decipol value of the perceived air quality ratings is determined by classifying the values into one of the values or ranges of values in the corresponding category in the above-mentioned matrix, resulting in three single scores.

Lastly, the mean value of the three single scores is calculated, which is a measure for the overall quantitative and qualitative odour characteristics of the airstream evaluated.

This single score is a specific numerical value allowing for an overall assessment of the odour characteristics.

When using the inventive olfactory method to evaluate the efficiency of a specific type of equipment used to remove VOCs or odours from an airstream, one specific score may be obtained by the inventive method for the odour characteristics of the air upstream of the equipment used, as well as one single score for the air downstream of the equipment used.

These scores obtained by the method of the present invention allow for a comparison of the used equipment, when used under the same conditions.

With this, the inventive method for the first time allows for a quantitative analysis of the odour characteristics of an airstream to be made alongside the qualitative odour assessment. This allows a direct comparison of various odour treatment methods.

Additionally, the method according to the present invention may be implemented on a computer system, wherein the first mean value of the results of ratings of acceptability of the odour and the second mean value of the results of the ratings of the odour intensity, as well as the decipol value of the ratings of the perceived air quality may be inputted. A computer programme adapted to perform the steps of the present invention automatically calculates the score which is then outputted as the result of the operated computer programme. With such a computer programme adapted to operate the inventive method, the assessment of odour characteristics according to the present invention may be done automatically and with less overall consumption in energy and time.

The present invention is now further illustrated by the following embodiment example, which is partly illustrated by the enclosed FIG. 1.

FIG. 1 shows an experimental test bench which may be used to obtain the ratings of hedonic tone, odour intensity and perceived air quality from the test panellists, for example, when using the inventive method for comparing the effectiveness of different types of equipment in odour removal. This experimental test bench is an optional further aspect of the present invention.

FIG. 1 shows at (1) a port where purified air with ambient temperature and a dewpoint of 12.5° C. is introduced into the test bench. The air is then passed through a furnace or heater (2) to heat the air to the required operating temperature for the test piece or equipment (4). Once the air has reached its operating temperature, the odourous challenge agent is added to the airflow at a dosing port (3). A concentration of the challenge agent in the airstream is predefined by determining the odour threshold among the panel group (50% of the group detect the agent's presence) The airstream is then dosed with three times the odour threshold concentration of the challenge agent.

The odourous airflow is then passed through the equipment or test piece (4). The temperature of the airflow is checked to ensure the operating temperature as is required.

The odourous airflow is ducted through a cooling area (5) to bring the airstream to ambient temperature. This ensures that there are no errors in the odour detection due to temperature influence.

The odourous airflow is then ducted to the sniffing port (6), where the panel members rate the odour using the panel test method outlined above, i.e., assessing values for the hedonic tone, the odour intensity and the perceived air quality on the given scales.

For comparison values, two valves (7) allow the test piece of equipment (4) to be bypassed for the odour measurement of the upstream, without treatment. A port (8) for taking samples for other measurement techniques such as GC-O, is integrated in the test set up. The placement of the sample port (8) is such that both untreated (upstream of test piece) and treated (downstream of test piece) samples may be taken.

The values given by the panellists for perceived air quality, hedonic tone intensity are scaled for the order levels required downstream of the odour removal equipment. This analysis method gives a score for the performance of the removal equipment in each of the three categories, thus allowing the overall average score to be calculated. The score is specific to each piece of the equipment and allows comparison of equipment when tested under the same conditions.

Table 1 below shows an exemplary matrix according to the inventive method containing ranges of values for each of the three rating categories being assigned to one score in a scale of scores.

TABLE 1

| | Category | | |
|---|---|---|---|
| Score | Perceived air quality (decipol) | Hedonic Tone | Intensity |
| 10 | 1–2.9 (*) | 4–3.1 (*) | 0–0.0 (*) |
| 8 | 3–4.9 (*) | 3–2.1 (*) | 1–1.9 (*) |
| 6 | 5–7.9 (*) | 2–1.1 (*) | 2–2.9 (*) |
| 4 | 8–10.9 (*) | 1–0.1 (*) | 3–3.9 (*) |
| 2 | 11–15 (*) | 0–(−0.0) (*) | 4–4.9 (*) |
| 0 | >15 (*) | <(−1) (*) | >5 (*) |

* Example values (may vary depending on the starting conditions).

Thus, classifying the three values obtained for the categories in the matrix, three scores may be determined, the calculated mean value of which yields an overall average score corresponding to an overall quantitative and qualitative odour characteristic of the airstream evaluated.

The invention claimed is:

1. An olfactory method for simultaneously assessing a quantity and a quality of odours in an airstream, comprising the steps of:
   a) determining a first mean value of results of ratings of an acceptability of an odour of a single airstream, rated by a group of test persons;
   b) determining a second mean value of results of ratings of an odour intensity done by the same group of test persons for the same odourous airstream;
   c) determining a decipol value of ratings of a perceived air quality according to the method of Fanger of the same odourous airstream, rated by the same group of test persons;
   d) providing a matrix containing all mathematically possible values of the acceptability of rating, the odour intensity rating and the decipol values of the perceived air quality, wherein each value or a range of values of one the three rating categories is assigned to one score in a scale of scores:
   e) determining a score for each of the values taken from steps a), b), and c) by classifying it into one of the values or ranges of values in a corresponding category in the matrix of step d), which results in three scores; and
   f) calculating a third mean value of the three scores, resulting in an overall average score corresponding to an overall quantitative and qualitative odour characteristics of the airstream evaluated.

2. The method according to claim 1, wherein the single airstream is comprised of air upstream an odour removal equipment.

3. The method according to claim 1, wherein the single airstream is comprised of air downstream an odour removal equipment.

4. The method according to claim 1, wherein the odour removal equipment is a VOC removing catalyst.

5. The method according to claim 1, implemented on a computer system.

* * * * *